US008236915B2

(12) United States Patent
Delis et al.

(10) Patent No.: US 8,236,915 B2
(45) Date of Patent: Aug. 7, 2012

(54) HYDROSILYLATION CATALYSTS

(75) Inventors: Johannes G. P. Delis, Bergen op Zoom (NL); Susan A. Nye, Feura Bush, NY (US); Kenrick M. Lewis, Flushing, NY (US); Keith J. Weller, Rensselaer, NY (US); Paul J. Chirik, Ithaca, NY (US); Aaron M. Tondreau, Ithaca, NY (US); Sarah Kathleen Russell, Ithaca, NY (US)

(73) Assignees: Momentive Performance Materials Inc., Albany, NY (US); Cornell University, Ithaca, NY (US)

( * ) Notice: Subject to any disclaimer, the term of this patent is extended or adjusted under 35 U.S.C. 154(b) by 59 days.

(21) Appl. No.: 12/832,627

(22) Filed: Jul. 8, 2010

(65) Prior Publication Data
US 2011/0009573 A1 Jan. 13, 2011

Related U.S. Application Data

(60) Provisional application No. 61/224,598, filed on Jul. 10, 2009.

(51) Int. Cl.
C08G 77/06 (2006.01)
(52) U.S. Cl. ............... 528/14; 528/19; 528/20; 528/25; 528/31; 502/150; 502/167; 502/200; 502/405; 502/415; 502/416
(58) Field of Classification Search ............... None
See application file for complete search history.

(56) References Cited

U.S. PATENT DOCUMENTS

| 3,159,601 A | 12/1964 | Ashby |
| 3,220,972 A | 11/1965 | Lamoreaux |
| 3,775,452 A | 11/1973 | Karstedt |
| 4,550,152 A * | 10/1985 | Faltynek .................. 528/15 |
| 5,331,075 A | 7/1994 | Sumpter et al. |
| 5,432,140 A | 7/1995 | Sumpter et al. |
| 5,866,663 A | 2/1999 | Brookhart et al. |
| 5,955,555 A | 9/1999 | Bennett |
| 6,103,946 A | 8/2000 | Brookhart, III et al. |
| 6,214,761 B1 | 4/2001 | Bennett |
| 6,281,303 B1 | 8/2001 | Lavoie et al. |
| 6,297,338 B1 | 10/2001 | Cotts et al. |
| 6,417,305 B2 | 7/2002 | Bennett |
| 6,423,848 B2 | 7/2002 | Bennett |
| 6,432,862 B1 | 8/2002 | Bennett |
| 6,451,939 B1 | 9/2002 | Britovsek et al. |
| 6,455,660 B1 | 9/2002 | Clutton et al. |
| 6,458,739 B1 | 10/2002 | Kimberley et al. |
| 6,458,905 B1 | 10/2002 | Schmidt et al. |
| 6,461,994 B1 | 10/2002 | Gibson et al. |
| 6,472,341 B1 | 10/2002 | Kimberley et al. |
| 6,620,895 B1 | 9/2003 | Cotts et al. |
| 6,657,026 B1 | 12/2003 | Kimberley et al. |
| 7,053,020 B2 | 5/2006 | De Boer et al. |
| 7,148,304 B2 | 12/2006 | Kimberley et al. |
| 7,161,005 B2 | 1/2007 | Schlingloff et al. |
| 7,247,687 B2 | 7/2007 | Cherkasov et al. |
| 7,268,096 B2 | 9/2007 | Small et al. |
| 7,442,819 B2 | 10/2008 | Ionkin et al. |
| 7,456,285 B2 | 11/2008 | Schlingloff et al. |
| 2002/0058584 A1 | 5/2002 | Bennett et al. |
| 2006/0263675 A1 | 11/2006 | Adzic et al. |
| 2007/0264189 A1 | 11/2007 | Adzic et al. |
| 2008/0262225 A1 | 10/2008 | Schlingloff et al. |
| 2008/0293878 A1 | 11/2008 | Funk et al. |
| 2009/0068282 A1 | 3/2009 | Schlingloff et al. |
| 2009/0296195 A1 | 12/2009 | Fontana et al. |

FOREIGN PATENT DOCUMENTS

| WO | WO02/088289 | 11/2002 |
| WO | WO03/042131 | 5/2003 |

OTHER PUBLICATIONS

"Synthesis of Aryl-Substituted Bis(imino)pyridine Iron Dinitrogen Complexes" authored by Russell et al. and published in Inorg Chem. (2010) 49, 2782-2792.*
Speier, J.L., Webster J.A. and Barnes G.H., J. Am. Chem. Soc. 79, 974-979 (1957).
Nesmeyanov. A.N. et al., Tetrahedron 1962, 17, 61-68.
Corey, J.Y. et al., J. Chem. Rev. 1999, 99, 175-292.
C. Randolph, M.S. Wrighton, J. Am. Chem. Soc. 108 (1986) 3366-3374.
Bart et al., J. Am. Chem. Soc., 2004, 126, 13794-13807.
Andrew M. Archer et al., Organometallics, 2006, 25, 4269-4278.
Kröll et al., Macromol. Chem. Phys. 2001, 202, No. 5, pp. 645-653.
Kim et al., Journal of Organometallic Chemistry 673 (2003) 77-83.
Bouwkamp et al., J. Am. Chem. Soc. 2006, 128, 13340-13341.
Russell et al., Inorg. Chem. 2010, 49, 2782-2792.
Tondreau et al., Organic Letters, 2008, vol. 10, No. 13, 2789-2792.
Cetinkaya et al., Journal of Molecular Catalysis A: Chemical 142 (1999) 101-112.
Figgins et al., J. Am. Chem. Soc. 1960, vol. 82, 820-824.
Britovsek et al., Chem. Commun., 1998, 849-850.
Haarman et al., Am. Chem. Soc., Organometallics 1997, 16, 54-67.
Lu et al., Inorganica Chimica Acta, 134 (1987) 229-232.
Albon et al., Inorganica Chimica Acta, 159 (1989) 19-22. Toma et al., J. Braz. Chem. Soc., vol. 7, No. 6, 391-394, 1996.
Abu-Surrah et al., Journal of Organometallic Chemistry 648 (2002) 55-61.
Lions et al., J. Chem. Soc. (A) 1957, vol. 79, 2733-2738.
Kickelbick et al., New J. Chem., 2002, 26, 462-468.
Kooistra et al., Inorganica Chimica Acta 357 (2004) 2945-2952.
Sacconi et al., J. Chem. Soc. (A), 1968, 1510-1515.
Alyea et al., Syn. React. Inorg. Metal-Org. Chem., 4(6), 535-544 (1974).
Steven D. Ittel et al., DuPont's Versipol®Late Metal Polymerization Catalysts, http://www.nacatsoc.org/18nam/Orals/044-Ittel-DuPont's%20Versipol%C2%AE%20Late%20Metal%20 Polymerization.pdf.
Beilstein Seach Results.

* cited by examiner

*Primary Examiner* — Marc Zimmer
(74) *Attorney, Agent, or Firm* — Dominick G. Vicari; Joseph S. Ostroff; Wiggin and Dana LLP

(57) ABSTRACT

Disclosed herein are manganese, iron, cobalt, or nickel complexes containing terdentate pyridine diimine ligands and their use as efficient and selective hydrosilylation catalysts.

38 Claims, No Drawings

HYDROSILYLATION CATALYSTS

CROSS REFERENCE TO RELATED APPLICATIONS

This application claims priority to U.S. provisional application No. 61/224,598, filed Jul. 10, 2009, which is herein incorporated by reference in its entirety.

FIELD OF THE INVENTION

This invention relates generally to transition metal-containing compounds, more specifically to manganese, iron, cobalt, or nickel complexes containing pyridine di-imine ligands and their use as efficient and selective hydrosilylation catalysts.

BACKGROUND OF THE INVENTION

Hydrosilylation chemistry, typically involving a reaction between a silyl hydride and an unsaturated organic group, is the basis for synthesis routes to produce commercial silicone-based products like silicone surfactants, silicone fluids and silanes as well as many addition cured products like sealants, adhesives, and silicone-based coating products. Heretofore, hydrosilylation reactions have been typically catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's-catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal complex catalysts are widely accepted as catalysts for hydrosilylation reactions, they have several distinct disadvantages. One disadvantage is that the precious metal complex catalysts are inefficient in catalyzing certain reactions. For example, in the case of hydrosilylations of allyl polyethers with silicone hydrides using precious metal complex catalysts, use of an excess amount of allyl polyether, relative to the amount of silicone hydride, is needed to compensate for the lack of efficiency of the catalyst in order to ensure complete conversion of the silicone hydride to a useful product. When the hydrosilylation reaction is completed, this excess allyl polyether must either be: (A) removed by an additional step, which is not cost-effective, or (B) left in the product which results in reduced performance of this product in end-use applications. Additionally, the use of an excess amount of allyl polyether typically results in a significant amount of undesired side products such as olefin isomers, which in turn can lead to the formation of undesirably odoriferous byproduct compounds.

Another disadvantage of the precious metal complex catalysts is that sometimes they are not effective in catalyzing hydrosilylation reactions involving certain type of reactants. It is known that precious metal complex catalysts are susceptible to catalyst poisons such as phosphorous and amine compounds. Accordingly, for a hydrosilylation involving unsaturated amine compounds, the precious metal catalysts known in the art are normally less effective in promoting a direct reaction between these unsaturated amine compounds with Si-hydride substrates, and will often lead to the formation of mixtures of undesired isomers.

Further, due to the high price of precious metals, the precious metal-containing catalysts can constitute a significant proportion of the cost of silicone formulations. Recently, global demand for precious metals, including platinum, has increased, driving prices for platinum to record highs, creating a need for effective, low cost replacement catalysts.

As an alternative to precious metals, recently, certain iron complexes have gained attention for use as hydrosilylation catalysts. Illustratively, technical journal articles have disclosed that that $Fe(CO)_5$ catalyzes hydrosilylation reactions at high temperatures. (Nesmeyanov, A. N. et al., Tetrahedron 1962, 17, 61), (Corey, J.Y et al., J. Chem. Rev. 1999, 99, 175), (C. Randolph, M. S. Wrighton, J. Am. Chem. Soc. 108 (1986) 3366). However, unwanted by-products such as the unsaturated silyl olefins, which are resulted from dehydrogenative silylation, were formed as well.

A five-coordinate Fe(II) complex containing a pyridine di-imine (PDI) ligand with isopropyl substitution at the ortho positions of the aniline rings has been used to hydrosilate an unsaturated hydrocarbon (1-hexene) with primary and secondary silanes such as $PhSiH_3$ or $Ph_2SiH_2$ (Bart et al., J. Am. Chem. Soc., 2004, 126, 13794) (Archer, A. M. et al. Organometallics 2006, 25, 4269). However, one of the limitations of these catalysts is that they are only effective with the aforementioned primary and secondary phenyl-substituted silanes, and not with, for example, tertiary or alkyl-substituted silanes such as $Et_3SiH$, or with alkoxy substituted silanes such as $(EtO)_3SiH$.

Other Fe-PDI complexes have also been disclosed. U.S. Pat. No. 5,955,555 discloses the synthesis of certain iron or cobalt PDI dianion complexes. The preferred anions are chloride, bromide and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. However, the catalysts and catalyst systems disclosed in these references are described for use in the context of olefin polymerizations and/or oligomerisations, not in the context of hydrosilylation reactions.

There is a continuing need in the hydrosilation industry for non-precious metal-based catalysts that are effective for efficiently and selectively catalyzing hydrosilylation reactions. The present invention provides one answer to that need.

SUMMARY OF THE INVENTION

In one aspect, the present invention is directed to a compound of Formula (I) or Formula (II)

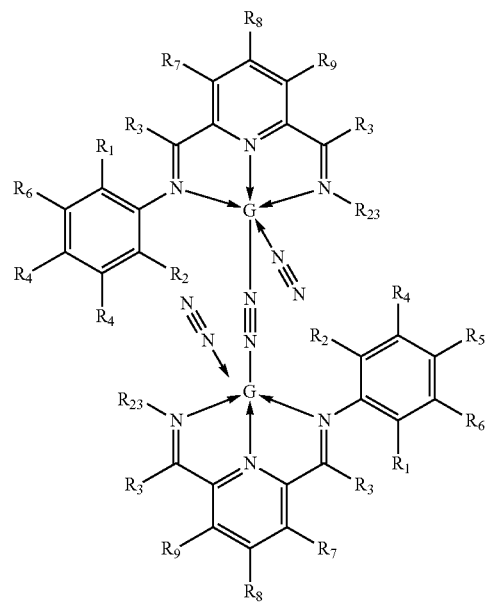

Formula (I)

-continued

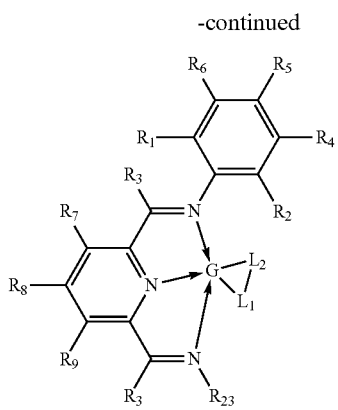

Formula (II)

wherein:

G is Mn, Fe, Ni, or Co;

each occurrence of $R_1$, $R_2$, $R_3$, $R_4$, $R_5$, $R_6$, $R_7$, $R_8$, and $R_9$ is independently hydrogen, C1-C18 alkyl, C1-C18 substituted alkyl, aryl, substituted aryl, or an inert functional group, wherein $R_2$-$R_9$, other than hydrogen, optionally contain at least one heteroatom;

each occurrence $R_{23}$ is independently C1-C18 alkyl, C1-C18 substituted alkyl, aryl or substituted aryl, wherein $R_{23}$ optionally contains at least one heteroatom;

optionally any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure;

$L_1$-$L_2$ is

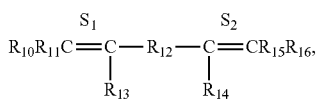

Formula (A)

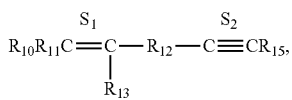

Formula (B)

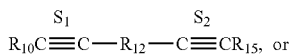

Formula (C)

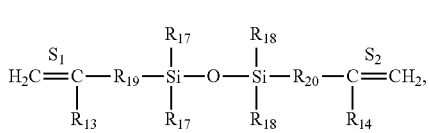

Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together may form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together may form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$, and $R_{20}$ optionally contain at least one heteroatom; wherein $L_1$-$L_2$ bonds with G through unsaturated sites S1 and S2.

In another aspect, the present invention is directed to a process for the hydrosilylation of a composition containing a silyl hydride and a compound containing at least one unsaturated group. The process includes: (i) contacting the composition with a metal complex of Formula (I), Formula (II), Formula (III) or Formula (IV), optionally in the presence of a solvent, to cause the silyl hydride to react with the compound containing at least one unsaturated group to produce a hydrosilylation product containing the metal complex; (ii) optionally removing the metal complex from the hydrosilylation product. Formula (III) is:

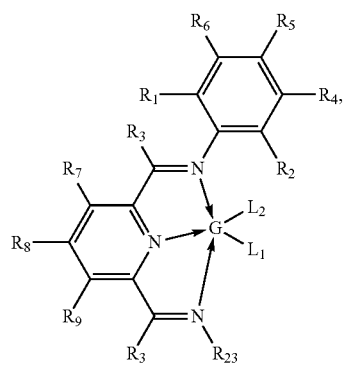

Formula (III)

and Formula (IV) is

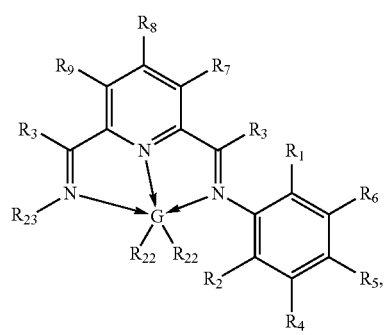

Formula (IV)

wherein

G is Mn, Fe, Ni, or Co;

each occurrence of $R_1$, $R_2$, $R_3$, $R_4$, $R_5$, $R_6$, $R_7$, $R_8$ and $R_9$ is independently H, C1-18 alkyl, C1-C18 substituted alkyl, aryl, substituted aryl, or an inert functional group, wherein $R_2$-$R_9$, other than hydrogen, optionally contain at least one heteroatom;

each occurrence of $R_{22}$ and $R_{23}$ is independently C1-C18 alkyl, C1-C18 substituted alkyl, aryl or substituted aryl group, wherein $R_{22}$ and $R_{23}$ optionally contain at least one heteroatom, preferably $R_{22}$ does not contain beta hydrogen (G-alpha C-beta C-beta hydrogen);

optionally any two of any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure, $L_1$ is $R_{10}R_{11}C$=$CR_{12}R_{13}$ or $R_{18}C$≡$CR_{19}$ and $L_2$ is $R_{14}R_{15}C$=$CR_{16}R_{17}$ or $R_{20}C$≡$CR_{21}$, wherein each occurrence of $R_{10}$-$R_{21}$ is independently hydrogen, C1-C18 alkyl, C1-C18 alkenyl, or C1-C18 alkynyl, wherein optionally $R_{18}$-$R_{19}$ and/or $R_{20}$-$R_{21}$, and/or any two of $R_{10}$, $R_{11}$, $R_{12}$, $R_{13}$ and/or any two of $R_{14}$, $R_{15}$, $R_{16}R_{17}$ taken together may form a ring being a substituted or unsubstituted, saturated, or unsaturated cyclic structure, wherein $R_{10}$-$R_{21}$, other than hydrogen, optionally contain at least one heteroatom, and $R_{10}$-$R_{21}$, other than hydrogen, are optionally substituted, and wherein $L_1$ and $L_2$ bond with G through unsaturated sites.

DETAILED DESCRIPTION OF THE INVENTION

In one embodiment of the invention, there is provided a complex of the Formulae (I), (II), (III) or (IV) as illustrated above. In connection with these formulae, G can be Mn, Fe, Ni, or Co in all the valence states. Preferably G is iron or cobalt. More preferably M is Fe, such as Fe (II) and Fe (III).

As used herein, "alkyl" includes straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

By "alkenyl" herein is meant any straight, branched, or cyclic alkenyl group containing one or more carbon-carbon double bonds, where the point of substitution can be either a carbon-carbon double bonds or elsewhere in the group. Specific and non-limiting examples of alkenyls include, but are not limited to, vinyl, propenyl, allyl, methallyl, ethylidenyl norbornane.

By "alkynyl" is meant any straight, branched, or cyclic alkynyl group containing one or more carbon-carbon triple bonds, where the point of substitution can be either at a carbon-carbon triple bond or elsewhere in the group.

By "unsaturated" is meant one or more double or triple bonds. In a preferred embodiment, it refers to carbon-carbon double or triple bonds.

By "inert functional group" herein is meant a group other than hydrocarbyl or substituted hydrocarbyl which is inert under the process conditions to which the compound containing the group is subjected. The inert functional groups also do not substantially interfere with any process described herein that the compound in which they are present may take part in. Examples of inert functional groups include halo (fluoro, chloro, bromo, and iodo), ether such as —$OR^{30}$ wherein $R^{30}$ is hydrocarbyl or substituted hydrocarbyl.

"Hetero atoms" herein is meant any of the Group 13-17 elements except carbon, and can include for example oxygen, nitrogen, silicon, sulfur, phosphorus, fluorine, chlorine, bromine, and iodine.

In some embodiments, the complexes disclosed herein include those of Formulae (I), (II), (III) and (IV) having the following substituents: (1) $R_{23}$ is

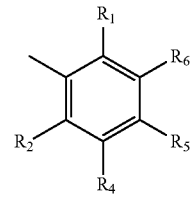

and/or (2) $R_1$ is hydrogen, methyl, ethyl, n-propyl or isopropyl; and/or (3) $R_1$ and $R_2$ are both methyl, ethyl, n-propyl or isopropyl groups; and/or (4) $R_3$ is methyl; and/or (5) $R_4$-$R_9$ are hydrogen; and/or (6) $R_{10}$, $R_{11}$, $R_{13}$, $R_{14}$, $R_{15}$, and $R_{16}$ are hydrogen; and/or (7) $R_{22}$ is —$CH_2SiR^{20}_3$, wherein each occurrence of $R^{20}$ is C1-C18 alkyl, C1-C18 substituted alkyl, aryl or substituted aryl, preferably $R^{20}$ is a methyl group.

In some embodiments, a complex according to Formula (II) is:

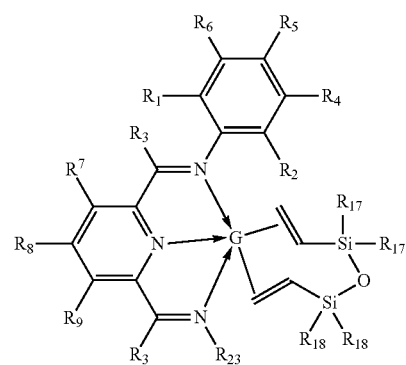

Formula (VI)

wherein G is Mn, Fe, Ni, or Co, each occurrence of $R_1$, $R_2$, $R_3$, $R_4$, $R_5$, $R_6$, $R_7$, $R_8$, and $R_9$ is independently hydrogen, C1-18 alkyl, C1-C18 substituted alkyl, aryl, substituted aryl, or an inert functional group, wherein $R_2$-$R_9$, other than hydrogen, optionally contain at least one heteroatom;

each occurrence of $R_{17}$ and $R_{18}$ is independently alkyl, substituted alkyl, aryl, or substituted aryl, wherein each of $R_{17}$ and $R_{18}$ optionally contains at least one heteroatom, wherein $R_{17}$ and $R_{18}$ taken together optionally form a ring being a substituted or unsubstituted, saturated, or unsaturated cyclic structure;

each occurrence of $R_{23}$ is independently C1-C18 alkyl, C1-C18 substituted alkyl, aryl or substituted aryl, wherein $R_{23}$ optionally contains at least one heteroatom;

optionally any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure.

The complexes represented by the structural Formula (VI) preferably have the following substituents: (1) $R_{23}$ is

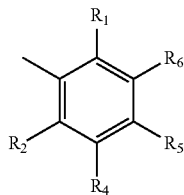

and/or (2) $R_1$ is hydrogen, methyl, ethyl, n-propyl or isopropyl; and/or (3) $R_1$ and $R_2$ are both methyl, ethyl, n-propyl or isopropyl groups; and/or (4) $R_3$ is methyl; and/or (5) $R_4$-$R_9$ are hydrogen; and/or (6) $R_{17}$ and $R_{18}$ are methyl groups.

A preferred complex according to Formula (VI) is represented by structural Formula (VII)

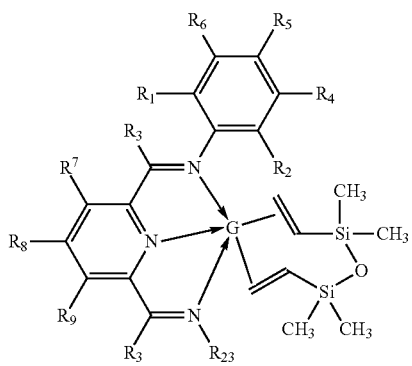

Formula (VII)

wherein G, $R_1$-$R_9$ and $R_{23}$ are as defined above in connection with Formula (VI).

In connection with Formula (II), $L_1$-$L_2$ typically contains at least two unsaturated sites per molecule. Further examples of $L_1$-$L_2$ include, but are not limited to, butadienes, 1,5-cyclooctadienes, dicyclopentadienes and norbornadienes.

In some embodiments, $L_1$-$L_2$ contains at least four unsaturated sites per molecule. In this circumstance, it is possible to form a metal-PDI dimer (PDI-metal-$L_1$-$L_2$-metal-PDI) with each metal bonding to two unsaturated sites of $L_1$-$L_2$. Exemplary $L_1$-$L_2$ for the metal-PDI dimer is tetravinyltetramethylcyclotetrasiloxane.

Various methods can be used to prepare complexes of Formula (I). In one embodiment of the invention, there is provided a process for the synthesis of a complex of Formula (I). The process includes the step of reacting a compound of Formula (V) with a reducing agent in the presence of nitrogen, wherein Formula (V) is

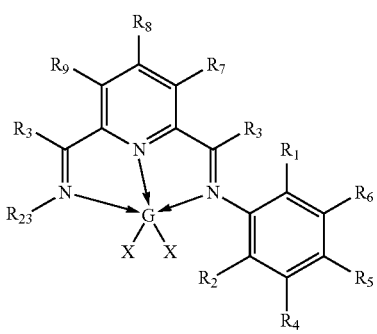

Formula (V)

wherein G is Mn, Fe, Ni, or Co;

each occurrence of $R_1$, $R_2$, $R_3$, $R_4$, $R_5$, $R_6$, $R_7$, $R_8$ and $R_9$ is independently H, C1-18 alkyl, C1-C18 substituted alkyl, aryl, substituted aryl, or an inert group, wherein $R_2$-$R_9$, other than hydrogen, optionally contain at least one heteroatom;

$R_{23}$ is C1-C18 alkyl group or C1-C18 substituted alkyl, aryl or substituted aryl group, wherein $R_{23}$ optionally contains at least one heteroatom;

optionally any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure, X is an anion, preferably F, Cl, Br, I, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group.

Preferably, the reducing agent has a reduction potential more negative than −0.6 v (versus ferrocene, as described in Chem. Rev. 1996, 96, 877-910. A larger negative number represents a larger reduction potential). The most preferred reducing agents have a reduction potential in the range of −2.8 to −3.1 v. An exemplary reducing agent includes, but is not limited to, sodium naphthalenide.

The methods to prepare the compounds represented by structural Formula (V) are known to a person skilled in the field. For example, the compounds of Formula (V) can be prepared by reacting a PDI ligand with a metal halide, such as $FeBr_2$. Typically, the PDI ligands are produced through condensation of an appropriate amine or aniline with 2,6-diacetylpyridine and its derivatives. If desired, the PDI ligands can be further modified by known aromatic substitution chemistry.

The complex of Formula (II) can be prepared by the step of reacting a complex of Formula (V) as defined above in the context of preparing the complex of Formula (I) with $L_1$-$L_2$, wherein $L_1$-$L_2$ is

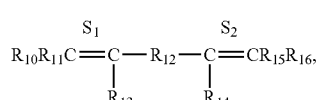

Formula (A)

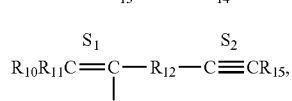

Formula (B)

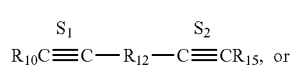

Formula (C)

-continued

Formula (D)

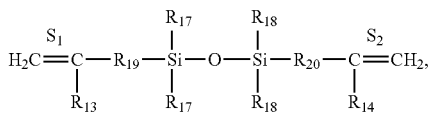

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, C2-C18 alkynyl, or aryl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted, each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom; wherein $R_{17}$ and $R_{18}$ taken together may form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$, and $R_{20}$ optionally contain at least one heteroatom.

Complexes of Formula (III) can be prepared by reacting a compound of Formula (V) such as PDIFeCl$_2$ with $L_1$ and $L_2$ as defined above in connection with Formula (III). Complexes of Formula (IV) may be prepared by reacting a compound of Formula (V) with alkylating agents, such as alkali metal salts, alkaline earth metal salts, Grignards, aluminum alkyls, mercury alkyls, and thallium alkyls.

As used herein, alkali metal salts include for example monoalkyl salts of lithium, sodium, potassium, rubidium and cesium. Alkaline earth metal salts include for example dialkyl salts of beryllium, magnesium, calcium, strontium and barium. Grignards suitable for the present invention include alkyl magnesium halides. Aluminum alkyls include for example trialkyl aluminum salts. Mercury alkyls refer to dialkyl mercury salts. Thallium alkyls include monoalkyl and trialkyl thallium salts.

The metal complexes of Formulae (I), (II), (III), (IV), (VI) and (VII) are useful for catalyzing industrially practiced hydrosilylation reactions. For example, (1) the crosslinking of silicone hydride fluids with terminally unsaturated polymers, and (2) hydrosilylation of terminally unsaturated amines with tertiary silanes. Accordingly, the metal complexes of the invention have utility in the preparation of useful silicone products, including, but not limited to, coatings, for example release coatings, room temperature vulcanizates, sealants, adhesives, products for agricultural and personal care applications, and silicone surfactants for stabilizing polyurethane foams.

When used as catalysts for the hydrosilylation reactions, the complexes of Formulae (I), (II), (III), (IV), (VI), and (VII) can be unsupported or immobilized on a support material, for example, carbon, silica, alumina, MgCl$_2$ or zirconia, or on a polymer or prepolymer, for example polyethylene, polypropylene, polystyrene, or poly(aminostyrene). The metal complexes can also be supported on dendrimers.

In some embodiments, for the purposes of attaching the metal complexes of the invention to a support, it is desirable that at least one of $R_1$ to $R_9$ of the metal complexes, preferably $R_6$, has a functional group that is effective to covalently bond to the support. Exemplary functional groups include but are not limited to SH, COOH, NH$_2$ or OH groups.

In one embodiment, silica supported catalyst may be prepared via Ring-Opening Metathesis Polymerization (ROMP) technology as discussed in the literature, for example Macromol. Chem. Phys. 2001, 202, No. 5, pages 645-653; Journal of Chromatography A, 1015 (2003) 65-71.

One way to immobilize catalysts on the surface of dendrimers is by the reaction of Si—Cl bonded parent dendrimers and functionalized PDI in the presence of a base is as illustrated by Kim et al. in Journal of Organometallic Chemistry 673 (2003) 77-83.

In one embodiment, the complexes of Formulae (I), (II), (III), (IV), (VI), (VII) are used as catalysts for the hydrosilylation of a composition containing a silyl hydride and a compound having at least one unsaturated group. The process includes contacting the composition with a metal complex of Formula (I), (II), (III), (IV), (VI) or (VII), either supported or unsupported, to cause the silyl hydride to react with the compound having at least one unsaturated group to produce a hydrosilylation product which may contain the metal complex catalyst. The hydrosilylation reaction can be conducted optionally in the presence of a solvent. If desired, when the hydrosilylation reaction is completed, the metal complex can be removed from the reaction product by magnetic separation and/or filtration.

The silyl hydride employed in the hydrosilylation reaction is not particularly limited. It can be any compound selected from the group consisting of $R_a SiH_{4-a}$, $(RO)_a SiH_{4-a}$, $Q_u T_v T_p^H D_w D^H_x M^H_y M_z$, and combinations thereof. The silyl hydride can contain linear, branched or cyclic structures, or combinations thereof. As used herein, each occurrence of R is independently C1-C18 alkyl, C1-C18 substituted alkyl, wherein R optionally contains at least one heteroatom, each occurrence of a independently has a value from 1 to 3, each of p, u, v, y and z independently has a value from 0 to 20, w and x are from 0 to 500, provided that p+x+y equals 1 to 500 and the valences of the all the elements in the silyl hydride are satisfied. Preferably, p, u, v, y, and z are from 0 to 10, w and x are from 0 to 100, wherein p+x+y equals 1 to 100.

As used herein, an "M" group represents a monofunctional group of formula $R'_3 SiO_{1/2}$, a "D" group represents a difunctional group of formula $R'_2 SiO_{2/2}$, a "T" group represents a trifunctional group of formula $R'SiO_{3/2}$, and a "Q" group represents a tetrafunctional group of formula $SiO_{4/2}$, an "$M^H$" group represents $H_g R'_{3-g} SiO_{1/2}$, a "$T^H$" represents $HSiO_{3/2}$, and a "$D^H$" group represents $R'HSiO_{2/2}$. As used herein, g is an integer from 0 to 3. Each occurrence of R' is independently C1-C18 alkyl, C1-C18 substituted alkyl, wherein R' optionally contains at least one heteroatom.

The compound containing an unsaturated group employed in the hydrosilylation reaction includes, but is not limited to, unsaturated polyethers such as alkyl-capped allyl polyethers, vinyl functionalized alkyl capped allyl or methylallyl polyethers; terminally unsaturated amines; alkynes; C2-C18 olefins, preferably alpha olefins; unsaturated cycloalkyl epoxide such as vinyl cyclohexyl epoxide; terminally unsaturated acrylates or methyl acrylates; unsaturated aryl ethers; unsaturated aromatic hydrocarbons; unsaturated cycloalkanes such as trivinyl cyclohexane; vinyl-functionalized polymer; and vinyl-functionalized silanes and vinyl-functionalized silicones.

Unsaturated polyethers suitable for the hydrosilylation reaction preferably are polyoxyalkylenes having the general formula:

(Formula VIII) or

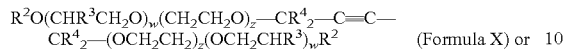
(Formula X) or

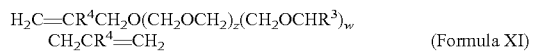
(Formula XI)

wherein $R^1$ denotes an unsaturated organic group containing from 2 to 10 carbon atoms such as allyl, methylallyl, propargyl or 3-pentynyl. When the unsaturation is olefinic, it is desirably terminal to facilitate smooth hydrosilylation. However, when the unsaturation is a triple bond, it may be internal. $R^2$ is hydrogen, vinyl, or a polyether capping group of from 1 to 8 carbon atoms such as the alkyl groups: $CH_3$, n-$C_4H_9$, t-$C_4H_9$ or i-$C_8H_{17}$, the acyl groups such as $CH_3COO$, t-$C_4H_9COO$, the beta-ketoester group such as $CH_3C(O)CH_2C(O)O$, or a trialkylsilyl group. $R^3$ and $R^4$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^4$ may also be hydrogen. Methyl is the most preferred $R^3$ and $R^4$ groups. Each occurrence of z is 0 to 100 inclusive and each occurrence of w is 0 to 100 inclusive. Preferred values of z and w are 1 to 50 inclusive.

The metal complexes of the invention are efficient and selective in catalyzing hydrosilylation reactions. For example, when the metal complexes of the invention are employed in the hydrosilylation of an alkyl-capped allyl polyether and a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. Further, when the compound containing an unsaturated group is unsaturated amine compound, the hydrosilylation product is essentially free of internal addition products and isomerization products of the unsaturated amine compound. As used herein, "essentially free" is meant no more than 10 wt %, preferably 5 wt % based on the total weight of the hydrosilylation product. "Essentially free of internal addition products" is meant that silicon is added to the terminal carbon.

The metal complexes of the invention can also be used in a process for preparing a silylated polyurethane, which includes the step of contacting terminally unsaturated polyurethane polymer with a silyl hydride in the presence of a complex of Formula (I), (II), (III), (IV), (VI), or (VII).

The following examples are intended to illustrate, but in no way limit the scope of the present invention. All parts and percentages are by weight and all temperatures are in degrees Celsius unless explicitly stated otherwise. All the publications and the U.S. patents referred to in the application are hereby incorporated by reference in their entireties.

EXAMPLES

General Considerations:

All air- and moisture-sensitive manipulations were carried out using standard vacuum line, Schlenk, and cannula techniques or in an MBraun inert atmosphere drybox containing an atmosphere of purified nitrogen. Solvents for air- and moisture-sensitive manipulations were initially dried and deoxygenated using literature procedures. See for example Pangborn et al., J. Organometallics 1996, 15, 1518.

The following abbreviations and terms are used:
bs—broad singlet
s—singlet
t—triplet
bm—broad multiple
GC—Gas Chromatography
MS—Mass Spectroscopy
THF—tetrahydrofuran Examples 1-9

Preparation of Metal Complexes of the Invention

Example 1

Preparation of [2,6-Diacetylpyridinebis(2,6-dimethylphenylimine)]iron dibromide (hereafter $^{2,6\text{-}Me2}$PDIFeBr$_2$)

1.1 Preparation of 2,6-diacetylpyridine

A 3 L 3-neck round bottomed flask was charged with 54.6 g (0.802 mol) of sodium ethoxide. While stirring vigorously with a mechanical stirrer, a solution of 35.5 g (0.159 mol) of 2,6-diethyl pyridinedicarboxylic ester in 300 mL of ethyl acetate was added dropwise to the flask. The resulting slurry was refluxed for 20 h, followed by cooling to 0° C., and addition of 350 mL (4.2 mol) of concentrated HCl. The mixture was then refluxed for 20 h, forming a white precipitate and a clear yellow solution. Upon cooling, the mixture was added to a separatory funnel containing ~1 L of water. The organic layer was separated; and the aqueous layer was extracted with $CH_2Cl_2$. The organic layers were combined, washed with saturated $Na_2CO_3$, dried over $Na_2SO_4$, and concentrated using rotary evaporation. The resulting brown solid was dissolved in a minimal amount of $CH_2Cl_2$ (30-50 mL), followed by the addition of an excess (~1 L) of pentane. A dark red-brown side-product was precipitated, and the solution was decanted. This solution was cooled to −78° C. and scraped to produce a tan solid. This was collected on a buchner funnel, and the filtrate repeatedly concentrated and crystallized to yield 16.7 g (65%, 0.102 mol) of the desired product.

1.2 Preparation of 2,6-Diacetylpyridinebis(2,6-dimethylphenylimine) (hereafter $^{2,6\text{-}Me2}$PDI)

A 250 mL round bottom flask was charged with 4.0 g of 2,6-diacetylpyridine, 6.09 g (2.05 eq.) of 2,6-dimethylaniline, and 100 mL of methanol. A catalytic amount of p-toluenesulfonic acid was added; and the reaction mixture was refluxed overnight into a Dean-Stark trap containing potassium sulfate. The reaction mixture was then cooled; and the methanol was reduced to approximately half of its starting volume. The mixture was cooled to −35° C. and the solid was filtered yielding 4.5 g (50%) of the desired product. The filtrate can be concentrated and cooled to yield more ligand.
$^1$H NMR (benzene-d$_6$, 20° C.): δ=8.50 (d, 2H, m-Py), 7.28 (t, 1H, p-Py)), 7.08 (d, 4H, m-Ar), 6.99 (t, 2H, p-Ar), 2.17 (s, 6H, $CH_3$), 2.05 (s, 12H, Ar—$CH_3$).

1.3 Preparation of $^{2,6\text{-}Me2}$PDIFeBr$_2$

A round bottom flask was charged with 2.0 grams of $^{2,6\text{-}Me2}$PDI and 1.16 g of FeBr$_2$, followed by 30 mL of THF. This mixture immediately turned dark blue, and was stirred overnight. The THF was then removed; and pentane was added. The slurry was filtered on a glass frit; and the solid was dried yielding 3.03 g (96%) of paramagnetic $^{2,6\text{-}Me2}$PDIFeBr$_2$. $^1$H NMR (benzene-d$_6$, 20° C.): δ=77.71, 52.48, 15.92, 14.80, −12.50, −22.37.

Example 2

Preparation of [($^{2,6\text{-}Me2}$PDI)Fe(N$_2$)]$_2$[μ-(N$_2$)]

In an inert atmosphere, to a 50 mL round bottom flask was added 500 mg (0.85 mmol) of ($^{2,6\text{-}Me2}$PDI)FeBr$_2$, 41 mg (1.79 mmol) of sodium, and 5 mg (0.04 mmol) of naphthalene. To the stirring mixture was added approximately 25 mL of THF. The reaction mixture was stirred until the sodium was completely consumed, about 2 hours, and the THF was removed in vacuo. Diethyl ether was added to the residue and the solution was filtered through Celite®. The volatiles were again removed and the solid was dissolved in a minimal amount of diethyl ether and recrystallized at −35° C. yielding 278 mg (70%) of the desired red brown compound. Elemental Analysis for C$_{50}$H$_{54}$N$_{12}$Fe: Calc. C, 64.25 wt %; H, 5.82 wt %; N, 17.98 wt %. Found C, 63.87 wt %; H, 6.19 wt %; N, 17.80 wt %. $^1$H NMR (benzene-d$_6$, 20° C.): δ=1.35 (bs, 24H, Ar CH$_3$), 1.78 (bs, 12H, C(CH$_3$)), 6.92 (bs, 12H, m- and p-Ar), 7.52 (bs, 2H, p-py), 8.10 (bs, 4H, m-py). $^{13}$C NMR (benzene-d$_6$, 20° C.): δ=16.17 (Ar CH$_3$), 19.50 (C(CH$_3$)), 115.92 (m- or p-py), 125.35 (m- or p-Ar), 130.93 (m- or p-Ar), 148.76 (m- or p-py), 153.05. $^{15}$N NMR (toluene-d$_8$, −80° C.) δ=−355.5 (bs), −334.2 (bs), −322.4 (bs). IR(toluene): ν(N$_2$)=2102, 2085 cm$^{-1}$.

Example 3

Preparation of [($^{2,6\text{-}Et2}$PDI)Fe(N$_2$)]$_2$[μ-(N$_2$)]

A procedure similar to that used for [($^{2,6\text{-}Me2}$PDI)Fe(N$_2$)]$_2$[μ-(N$_2$)] was followed using 500 mg (0.78 mmol) of $^{2,6\text{-}Et2}$PDIFeBr$_2$, 38 mg (1.64 mmol) of sodium, and 5 mg (0.04 mmol) of naphthalene. Approximately 305 mg (79%) of a red brown product was obtained. Elemental Analysis for C$_{58}$H$_{70}$N$_{12}$Fe$_2$: Calc. C, 66.54 wt %; H, 6.74 wt %; N, 16.05 wt %. Found C, 66.27 wt %; H, 7.10 wt %; N, 15.65 wt %. $^1$H NMR (benzene-d$_6$, 20° C.): δ=0.72 (bs, 24H, CH$_2$CH$_3$), 1.65 (bs, 28H, C(CH$_3$)) and CH$_2$CH$_3$), 7.04 (bm, 12H, m- and p-Ar), 7.64 (bs, 2H, p-py), 8.16 (bs, 4H, m-py). $^{13}$C NMR (benzene-d$_6$, 20° C.): δ=14.79 (CH$_2$CH$_3$), 18.07 (C(CH$_3$)), 24.68 (CH$_2$CH$_3$), 117.04 (m- or p-py), 125.77 (m- or p-Ar), 126.19 (m- or p-Ar), 135.94 (m- or p-py). $^{15}$N NMR (toluene-d$_8$, −80° C.) δ=−356.7 (bs), −331.5 (bs), −324.1 (bs). IR (toluene): ν(N$_2$)=2101, 2086 cm$^{-1}$.

Example 4

Preparation of [2,6-Diacetylpyridinebis(2,6-dimethylphenylimine)]Iron (1,1'-Divinyltetramethyldisiloxane) [hereafter ($^{2,6\text{-}Me2}$PDI)Fe(1,1'-Divinyltetramethyldisiloxane)]

In an inert atmosphere, to a 50 mL round bottom flask was added 500 mg (0.85 mmol) of ($^{2,6\text{-}Me2}$PDI)FeBr$_2$, 41 mg (1.79 mmol) of sodium, and 5 mg (0.04 mmol) of naphthalene. To the stirring mixture was added approximately 25 mL of THF. The reaction mixture was stirred until the sodium was completely consumed, about 2 hours, and 475 mg (2.55 mmol) of 1,1'-divinyltetramethyldisiloxane was added to the solution. The THF and excess vinyl silane were removed on a high vacuum line; and ether was added to the residue. The solution was filtered through Celite®. The volatiles were removed and the solid was recrystallized from ether yielding 460 mg (88%) of a dark red paramagnetic powder that gave broad peaks in the $^1$H NMR spectrum. $^1$H NMR (benzene-d$_6$, 20° C.): δ=171.22, 36.99, 6.00, 2.11, 0.69, 0.16, −4.24, −18.34, −112.68.

Example 5

Alternative Preparation of ($^{2,6\text{-}Me2}$PDI)Fe(1,1'-Divinyltetramethyldisiloxane)

In an inert atmosphere, to a diethyl ether solution of 100 mg (0.11 mmol) of [($^{2,6\text{-}Me2}$PDI)Fe(N$_2$)]$_2$[μ-(N$_2$)] was added 60 mg (0.32 mmol) of 1,1'-divinyltetramethyldisiloxane. The addition was accompanied by gas evolution and a color change of the solution to red. The volatiles were removed and the residue was crystallized from the addition of a small amount of pentane. The yield was 95 mg (72%).

Example 6

Preparation of [2,6-Diacetylpyridinebis(2-isopropylphenylimine)]iron(1,1'-Divinyltetramethyldisiloxane) [hereafter ($^{2\text{-}iPr}$PDI)Fe(1,1'-Divinyltetramethyldisiloxane)]

The procedure similar to that of ($^{2,6\text{-}Me2}$PDI)Fe(1,1'-Divinyltetramethyldisiloxane) was followed with 418 mg (0.68 mmol) of ($^{2\text{-}iPr}$PDI)FeBr$_2$, 33 mg (1.43 mmol) of sodium, 5 mg (0.04 mmol) of naphthalene, and 381 mg (2.04 mmol) 1,1'-divinyltetramethyldisiloxane. Approximately 309 mg (71%) of a dark purple powder was obtained. This compound exhibits an $^1$H NMR spectrum that has broadened peaks but a rather narrow range, and seems most consistent with at least two isomers of the compound, most likely the C$_2$ and C$_s$ symmetric molecules. $^1$H NMR (benzene-d$_6$, 20° C.): δ=−5.76, −2.30, 0.10, 0.58, 0.87, 0.99, 1.25, 2.52, 2.70, 3.25, 3.94, 4.45, 4.52, 5.62, 5.84, 6.09, 6.53, 8.30, 10.51.

Example 7

Preparation of Bis[(trimethylsilyl)methyl]iron[2,6-diacetylpyridinebis(2-methylphenylimine) [hereafter ($^{2,6\text{-}Me2}$PDI)Fe(CH$_2$SiMe$_3$)$_2$]

In an inert atmosphere, a 20 mL scintillation vial was charged with 0.443 g (1.00 mmol) of ($^{2,6\text{-}Me2}$PDI)FeCl$_2$. Pentane (~10 mL) was added forming a slurry. The solution was cooled to −35° C. for approximately 30 minutes after which time a pentane solution of LiCH$_2$SiMe$_3$ (0.188 g, 2.00 mmol) was added dropwise. The yellow slurry turned dark purple as it warmed. The reaction was stirred for 1-2 hours at room temperature, then it was filtered through Celite® and the solution was transferred into a new 20 mL scintillation vial. A pentane slurry of $^{2,6\text{-}Me2}$PDI (0.379 g, 1.00 mmol) was added dropwise to the stirring solution. The purple solution immediately turned dark violet. This mixture was stirred for 1-2 hours at room temperature. The mixture was then cooled to −35° C. and filtered to afford 0.425 g (71%) of ($^{2,6\text{-}Me2}$PDI)Fe(CH$_2$SiMe$_3$)$_2$ as a paramagnetic dark purple crystalline solid.

Example 8

Preparation of [2,6-Diisopropyl-N-{(E)-1-[6-{[(1R)-1-1-tert-butyl ethyl]ethanimidoyl}-2-pyridinyl]ethylidene}aniline]iron dibromide

8.1 Preparation of 1-{6-[(2,6-Diisopropylphenyl)ethanimidoyl]-2-pyridinyl}-1-ethanone A 250 mL round bottom flask was charged with 5.00 g (30.64 mmol) of 2,6-diacetylpyridine, 6.00 g (33.84 mmol) of 2,6-diisopropylaniline, and 100 mL of methanol. A catalytic amount of p-toluenesulfonic acid was added and the reaction mixture was refluxed overnight. The reaction mixture was then cooled to approximately 35° C. to 40° C. and filtered to remove 2,6-bis[1-(2,6-diisopropylphenylimino)ethyl]pyridine. The reaction solution was then placed at 0° C. for 24 hours, and the solid was filtered, yielding 4.25 g (43%) of the desired product as a yellow powder. $^1$H NMR (benzene-d$_6$, 20° C.): δ=1.21-1.14 (2 d, 12H, CH$_2$CH$_3$), 2.19 (s, 3H, CH$_3$), 2.52 (s, 3H, CH$_3$), 2.88 (sep, 2H, CH$_2$CH$_3$), 7.05-7.13 (m, 3H, Ar) and CH$_2$CH$_3$), 7.21 (t, 1H, p-py), 7.94 (d, 1H, py), 8.45 (d, 1H, py).

8.2 Preparation of 2,6-Diisopropyl-N-[(E)-1-(6-{[(1R)-1-tert-butyl ethyl]ethanimidoyl}-2 pyridinyl)ethylidene]aniline A round bottom flask was charged with 3.10 grams (9.61 mmol) of 1-{6-[(2,6-diisopropylphenyl)ethanimidoyl]-2-pyridinyl}-1-ethanone, 1.5 g of (R)-(−)-2-amino-3-methylbutane (1.5 eq.), 100 mL of methanol, and a catalytic amount of p-toluenesulfonic acid. The solution was refluxed overnight into a Dean-Stark trap containing sodium sulfate and then cooled to 0° C. and filtered. The white powder was washed with cold methanol and dried on a high vacuum line overnight yielding 2.95 g (76%) of the desired compound. $^1$H NMR (benzene-d$_6$, 20° C.): δ=0.96 (s, 9H, $^t$Bu), 1.08-1.16 (2 dd, 12H, CH$_2$CH$_3$), 2.20 (s, 3H, CH$_3$), 2.25 (s, 3H, CH$_3$), 2.88 (2 sep, 2H, CH$_2$CH$_3$), 2.94 (s, 3H, $^t$Bu-CHCH$_3$), 3.30 (q, 1H, $^t$Bu-CH—CH$_3$), 7.11-7.16 (m, 3H, Ar), 7.21 (t, 1H, p-py), 8.28 (d, 1H, py), 8.39 (d, 1H, py).

8.3 Preparation of [2,6-Diisopropyl-N-{(E)-1-[6-{[(1R)-1-1-tert-butyl ethyl]ethanimidoyl}-2-pyridinyl]ethylidene}aniline]iron dibromide In an inert atmosphere, a round bottom flask was charged with 2.5 g (6.61 mmol) of 2,6-diisopropyl-N-{(E)-1-[6-{[(1R)-1-tert-butyl ethyl]ethanimidoyl}-2-pyridinyl]ethylidene}aniline, 1.33 g (6.60 mmol) of FeBr$_2$ and 50 mL of THF. The reaction was stirred for twelve hours, at which time an equal volume of pentane was added resulting in the precipitation of the desired product which was collected on a sintered glass frit and dried under reduced pressure to yield 3.6 g (94%) of a blue paramagnetic powder. $^1$H NMR (CD$_2$Cl$_2$, 20° C.): δ=−19.43, −15.21, −11.97, −7.08, −4.52, −2.59, −1.40, 5.47, 14.51, 16.52, 23.15, 44.85, 70.32, 83.38, 187.03.

Example 9

Preparation of $^{2,6\text{-}Pr2}$PDIFe(butadiene) using (THF)$_2$Mg(Butadiene) as the reductant A procedure similar to that used for $^{2,6\text{-}Me2}$FePDIBr$_2$ as shown in example 1 was followed to make $^{2,6\text{-}iPr2}$FePDIBr$_2$. In an inert atmosphere, a scintillation vial containing 0.200 g (0.29 mmol) $^{2,6\text{-}iPr2}$PDIFeBr$_2$ and 0.095 g (0.43 mmol, 1.5 eq.) of (THF)$_2$Mg(Butadiene) was placed on a stir plate with a stir bar. While stirring, 10 mL of diethyl ether was added, yielding a red solution. The reaction was stirred for ten minutes, at which time 5 mL of pentane was added and the reaction mixture was filtered through Celite®. The volatiles were removed, and the residue was taken up into a minimum amount of diethyl ether and placed in a freezer at 35° C. for 12 hours. Filtration left 0.120 g (70%) of a red powder identified as $^{2,6\text{-}iPr2}$PDIFe(butadiene) on the filter frit.

Examples 10-14

Hydrosilylation Reactions Employing the Metal Complexes of the Invention

Example 10

Crosslinking of M$^{vi}$D$_{120}$M$^{vi}$ and MD$_{15}$D$^H_{30}$M

In an inert atmosphere, to a scintillation vial was added 1.0 g of M$^{vi}$D$_{120}$M$^{vi}$, in which M$^{vi}$ is vinyl dimethyl SiO$_{2/2}$, and 44 mg of MD$_{15}$D$^H_{30}$M. Another vial was prepared containing a stock solution of 2 mg of [($^{2,6\text{-}Me2}$PDI)Fe(N$_2$)]$_2$[μ-(N$_2$)] dissolved in 200 mg of ether. The catalyst solution was added at once to a stirring solution of 1 gram of 1.0 g of M$^{vi}$D$_{120}$M$^{vi}$ and 44 mg of MD$_{15}$D$^H_{30}$M. Almost immediately the solution gelled and became a solid. This gellation was indistinguishable from that observed for the reaction that uses the same silyl hydride and the unsaturated compound but employing a conventional platinum catalyst.

Example 11

Hydrosilylation of 1-Octene with Methylbis(trimethylsilyloxy)silane (MD$^H$M)

In a nitrogen filled drybox, to a scintillation vial was added 150 mg (1.33 mmol) of 1-octene and 229 mg (1.03 mmol) of MD$^H$M. To a separate vial was added 5 mg of [($^{2,6\text{-}Me2}$PDI)Fe(N$_2$)]$_2$[μ-(N$_2$)] and 200 mg of toluene. To the stirring solution of olefin and silane was added 19 mg of the catalyst solution (0.48 mg, 0.1 mole % to silane). The reaction was allowed to stir at room temperature in the drybox for about 1 hour. The resonance associated with the Si—H in the $^1$H NMR was observed to disappear during the course of the reaction, and a new resonance upfield at 0.41 ppm assignable to methylene attached to silicon appeared, giving a spectrum consistent with that of the previously reported compound.

Gas chromatography was performed on a Shimadzu GC-2010 gas chromatograph. GC analyses were performed using a Supelco 30 m×0.25 mm BETA DEX 120 capillary column. Temperature program for the reaction of MD$^H$M and 1-octene was as follows: 80° C., 2 min.; 15° C./min to 180° C., 2 min. The retention time of the hydrosilylated product was 7.83 minutes.

Example 12

Hydrosilylation of 1-Octene with Triethoxysilane

In a nitrogen filled atmosphere, to a scintillation vial was added 150 mg (1.33 mmol) of 1-octene and 170 mg (1.03 mmol), of triethoxysilane. To a separate vial was added 5 mg of [($^{2,6\text{-}Me2}$PDI)Fe(N$_2$)]$_2$[μ-(N$_2$)] and 200 mg of toluene. To the stirring solution of olefin and silane was added 19 mg of the catalyst solution (0.48 mg, 0.1 mole % to silane). The reaction was allowed to stir at room temperature in the drybox for about one hour. The resonance associated with the Si—H in the $^1$H NMR was observed to disappear during the course of the reaction, and a new resonance upfield at 0.62 ppm assignable to methylene attached to silicon appeared, giving a spectrum consistent with that of the previously reported compound.

Example 13

Procedure for the Hydrosilylation of Methyl Capped Allyl Polyether having nominal structure $H_2C$=$CHCH_2O(C_2H_4O)_8CH_3$ with Methylbis(trimethylsilyloxy)silane ($MD^HM$)

In a nitrogen filled drybox, a scintillation vial was charged with 1.00 g of methyl capped allyl polyether having nominal structure $H_2C$=$CHCH_2O(C_2H_4O)_8CH_3$ (2.09 mmol) and 0.465 g (2.09 mmol) of $MD^HM$, in which $M$=$(CH_3)_3SiO_{1/2}$ and $D^H$=$CH_3SiHO$. To the stirring solution of polyether and silane was added 10 mg (0.01 mmol) of $[(^{2,6-Me}PDI)Fe(N_2)][\mu-(N_2)]$. The scintillation vial was sealed and removed from the drybox and placed in a 60° C. oil bath. The reaction was stirred for 1 hour, at which time the vial was removed from the oil bath and the reaction was quenched by the addition of moist ether. The solution was analyzed by $^1$H NMR spectroscopy. The spectra established that the starting material methyl capped allyl polyether resonances were absent and resonances for the hydrosilylated product were present. There was no indication of propenyl resonances formed in the reaction within the detection limits of $^1$H NMR spectroscopy. The resonance associated with the Si—H in the $^1$H NMR was observed to disappear during the course of the reaction, and a new resonance upfield at 0.41 ppm assignable to methylene attached to silicon appeared, indicating the formation of the desired hydrosilylated product.

Example 14

Hydrosilylation of 1-Octene with Methylbis(trimethylsilyloxy)silane ($MD^HM$) using ($^{2,6-iPr2}PDI$)Fe(1,1'-Divinyltetramethyldisiloxane)

In a nitrogen filled drybox, to a scintillation vial was added 150 mg (1.33 mmol) of 1-octene and 229 mg (1.03 mmol) of $MD^HM$. To a separate vial was added 2 mg of ($^{2,6-iPr2}PDI$)Fe(1,1'-divinyltetramethyldisiloxane) and 200 mg of toluene. To the stirring solution of olefin and silane was added the catalyst solution (0.5 mole % to silane). The reaction was allowed to stir at room temperature in the drybox for 1 hour. The resonance associated with the Si—H in the $^1$H NMR was observed to disappear during the course of the reaction, and a new resonance upfield at 0.41 ppm assignable to methylene attached to silicon appeared, giving a spectrum consistent with that of the previously reported compound.

Comparative Example 1

Hydrosilylation of methyl capped allyl polyether ($H_2C$=$CHCH_2O(C_2H_4O)_8CH_3$) with $MD^HM$ using a conventional platinum catalyst The allylpolyether was a commercial methyl-capped sample with nominal structure $H_2C$=$CHCH_2O(C_2H_4O)_8CH_3$. The hydridosiloxane was bis(trimethylsiloxy)methylsilane, abbreviated $MD^HM$, in which $M$=$(CH_3)_3SiO_{1/2}$ and $D^H$=$CH_3SiHO$. 55.1 g polyether (0.13 mole) and 22.2 g $MD^HM$ (0.1 mole) were used in the hydrosilylation.

The reaction was performed in a 250 ml 4-necked round bottom flask fitted with a mechanical stirrer, water-cooled Friedrich condenser, heating mantle and temperature controller, and a sparge tube connected to a dry nitrogen source. The flask was purged with nitrogen prior to and after addition of the reagents. The reaction mixture was stirred and heated to 80° C., at which point the nitrogen sparge was discontinued and the reaction was catalyzed with 0.4 cc of a 10 mg Pt/ml solution of chloroplatinic acid in ethanol. A 20° C. temperature increase was observed after ~2 minutes and the reaction mixture changed from creamy opaque to a clear amber color. Heating was discontinued and stirring continued for another hour until the reaction mixture had cooled to 23° C. The test for SiH was negative. Completeness of utilization of the hydridosiloxane was determined by measuring the volume of $H_2$ produced when the reaction mixture was treated with alcoholic KOH as described by A. L. Smith, Analysis Of Silicones, John Wiley and Sons, NY 1974, pp 145-149. $^1$H NMR analysis confirmed the absence of SiH functionality in the product and $^{13}$C NMR showed the presence of propenyl ($^{13}$C=8.1 & 11.4 ppm) and allyl ($^{13}$C=115.6 & 133.8 ppm).

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A complex of Formula (I)

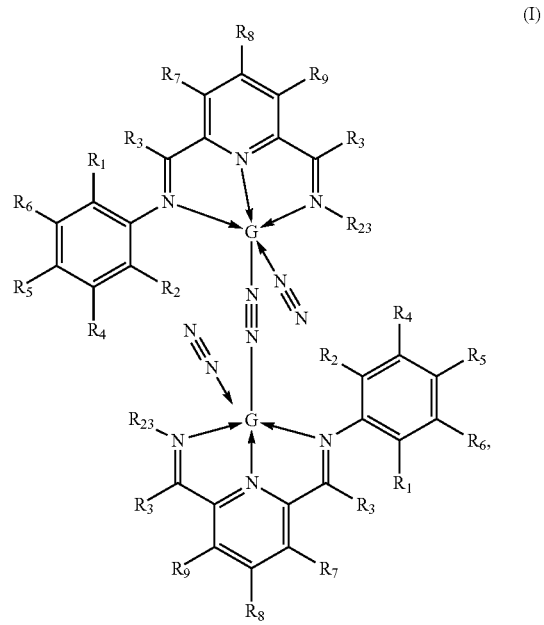

or Formula (II)

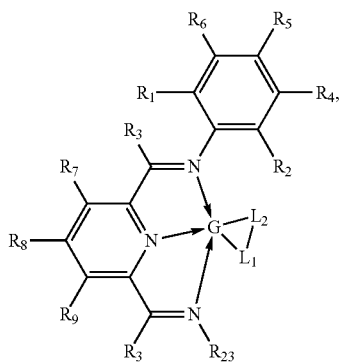

wherein:
G is Mn, Fe, Ni, or Co;
each occurrence of $R_1$, $R_2$, $R_3$, $R_4$, $R_5$, $R_6$, $R_7$, $R_8$, and $R_9$ is independently hydrogen, C1-18 alkyl, C1-C18 substituted alkyl, aryl, substituted aryl, or an inert functional group, wherein $R_2$-$R_9$, other than hydrogen, optionally contain at least one heteroatom;
each occurrence of $R_{23}$ is independently C1-C18 alkyl, C1-C18 substituted alkyl, aryl or substituted aryl, wherein $R_{23}$ optionally contains at least one heteroatom;
optionally any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure;
$L_1$-$L_2$ is

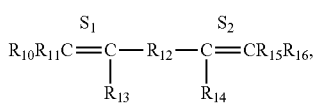 Formula (A)

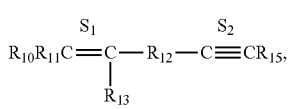 Formula (B)

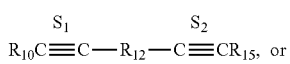 Formula (C)

Formula (D)

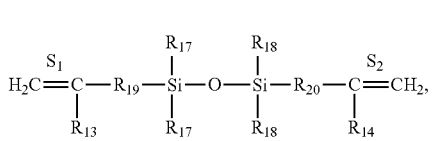

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted,
each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;
each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;
each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom;
wherein $L_1$-$L_2$ bonds with G through unsaturated sites $S_1$ and $S_2$;
with the proviso that
(1) $R_1$ in Formula (I) is hydrogen, methyl, ethyl or n-propyl; and
(2) $L_1$-$L_2$ of Formula (A) is selected from the group consisting of 1,5-cyclooctadienes, dicyclopentadienes, and norbornadienes.

2. A complex according to Formula (I) or Formula (II) of claim 1 wherein $R_{23}$ is

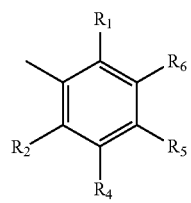

wherein $R_1$, $R_2$, $R_4$, $R_5$ and $R_6$ are as defined in claim 1.

3. A complex according to Formula (I) or Formula (II) of claim 1 wherein $R_1$ and $R_2$ in Formula (I) are both methyl, ethyl or n-propyl groups, and $R_1$ and $R_2$ in Formula (II) are both methyl, ethyl, n-propyl or isopropyl groups.

4. A complex according to Formula (I) or Formula (II) of claim 1 wherein $R_3$ is methyl.

5. A complex according to Formula (I) or Formula (II) of claim 1 wherein $R_{10}$, $R_{11}$, $R_{13}$, $R_{14}$, $R_{15}$, and $R_{16}$ are hydrogen.

6. A complex according to Formula (II) of claim 1 being

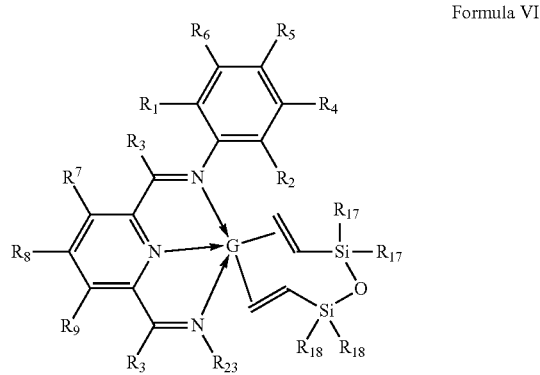

Formula VI wherein G, $R_1$-$R_9$, $R_{17}$, $R_{18}$ and $R_{23}$ are as defined in claim 1.

7. A complex according to Formula (II) of claim 1 being

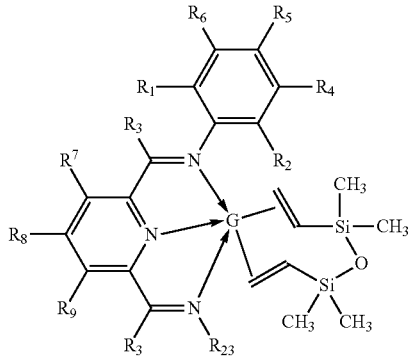

Formula VII wherein G, $R_1$-$R_9$ and $R_{23}$ are as defined in claim 1.

8. A complex according to Formula (II) of claim 1 wherein $L_1$-$L_2$ is an organosiloxane having at least four unsaturated sites, and wherein the complex is a dimer.

9. A complex according to Formula (I) or Formula (II) of claim 1 wherein G is Fe.

10. A complex according to Formula (I) of claim 1 or Formula (II) wherein the complex is immobilized on a support, and wherein Formula (II) is

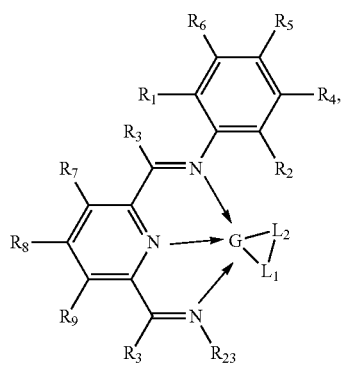

(II)

wherein:

G is Mn, Fe, Ni, or Co;

each occurrence of $R_1$, $R_2$, $R_3$, $R_4$, $R_5$, $R_6$, $R_7$, $R_8$, and $R_9$ is independently hydrogen, C1-18 alkyl, C1-C18 substituted alkyl, aryl, substituted aryl, or an inert functional group, wherein $R_2$-$R_9$, other than hydrogen, optionally contain at least one heteroatom:

each occurrence of $R_{23}$ is independently C1-C18 alkyl, C1-C18 substituted alkyl, aryl or substituted aryl, wherein $R_{23}$ optionally contains at least one heteroatom;

optionally any two of $R_1$, $R_2$, $R_3$, $R_4$, $R_5$, $R_6$, $R_7$, $R_8$, $R_9$ and $R_{13}$ vicinal to one another taken together may form a ring being a substituted or unsubstituted, saturated, or unsaturated cyclic structure;

$L_1$-$L_2$ is

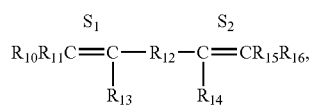

Formula (A)

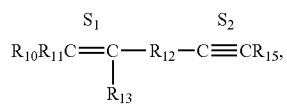

Formula (B)

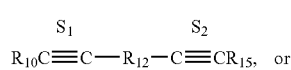

Formula (C)

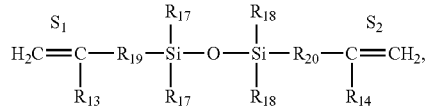

Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted, each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom;

wherein $L_1$-$L_2$ bonds with G through unsaturated sites $S_1$ and $S_2$.

11. The complex of claim 10 wherein the support is selected from the group consisting of carbon, silica, alumina, $MgCl_2$, zirconia, polyethylene, polypropylene, polystyrene, poly(aminostyrene), dendrimers, and combinations thereof.

12. The complex of claim 10 wherein at least one of $R_1$-$R_9$ contains a functional group that covalently bonds with the support.

13. A complex according to Formula (I) of claim 1 wherein $R_2$ is hydrogen, methyl, ethyl or isopropyl.

14. A process for the hydrosilylation of a composition containing a silyl hydride and a compound containing at least one unsaturated group, the process comprising: (i) contacting the composition with a complex according to Formula (I) of claim 1, or a complex of Formula (II), (III), or (IV), optionally in the presence of a solvent, to cause the silyl hydride to react with the compound containing at least one unsaturated group to produce a hydrosilylation product containing said complex, and (ii) optionally removing the complex from the hydrosilylation product, wherein
Formula (II) is:

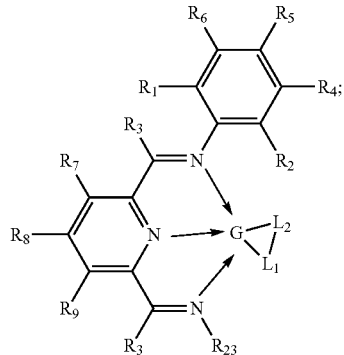
(II)

Formula (III) is:

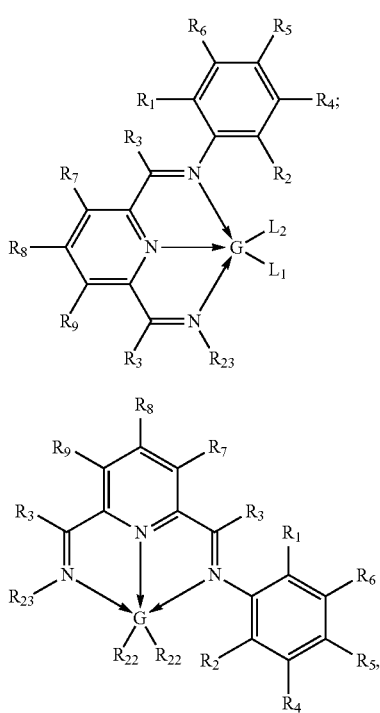
(III)

(IV)

wherein
G is Mn, Fe, Ni, or Co;
each occurrence of $R_1$, $R_2$, $R_3$, $R_4$, $R_5$, $R_6$, $R_7$, $R_8$ and $R_9$ is independently H, C1-18 alkyl, C1-C18 substituted alkyl, aryl, substituted aryl, or an inert functional group, wherein $R_2$-$R_9$, other than hydrogen, optionally contain at least one heteroatom;
each occurrence of $R_{22}$ and $R_{23}$ is independently C1-C18 alkyl, C1-C18 substituted alkyl, aryl or substituted aryl group, wherein $R_{22}$ and $R_{23}$ optionally contain at least one heteroatom;
optionally any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure;

$L_1$-$L_2$ is

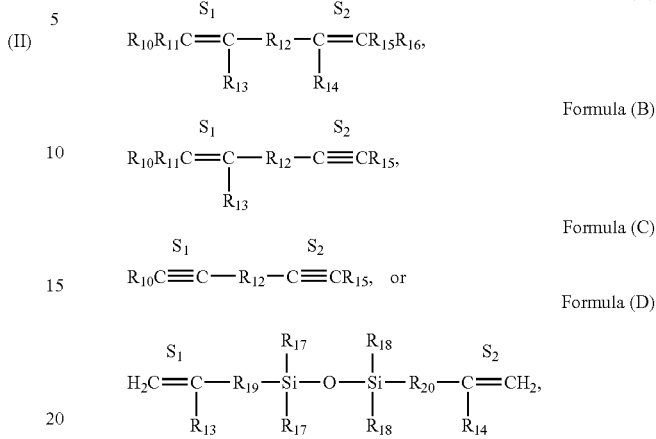

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted,
each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, substituted aryl, wherein $R_{12}$ optionally contains at least one heteroatom;
optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;
each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;
each occurrence of $R_{19}$ and $R_{20}$ is independently a covalent bond that connects Si and C, an alkyl, substituted alkyl, or a heteroatom, wherein $R_{19}$ and $R_{20}$ optionally contain at least one heteroatom;
wherein $L_1$-$L_2$ bonds with G through unsaturated sites $S_1$ and $S_2$;
$L_1$ is $R_{10}R_{11}C\!=\!CR_{12}R_{13}$ or $R_{18}C\!\equiv\!CR_{19}$ and $L_2$ is $R_{14}R_{15}C\!=\!CR_{16}R_{17}$ or $R_{20}C\!\equiv\!CR_{21}$, wherein each occurrence of $R_{10}$-$R_{21}$ is independently hydrogen, C1-C18 alkyl, C1-C18 alkenyl, or C1-C18 alkynyl, wherein optionally $R_{18}$-$R_{19}$ and/or $R_{20}$-$R_{21}$, and/or any two of $R_{10}$, $R_{11}$, $R_{12}$, $R_{13}$ and/or any two of $R_{14}$, $R_{15}$, $R_{16}R_{17}$ taken together may form a ring being a substituted or unsubstituted, saturated, or unsaturated cyclic structure, wherein $R_{10}$-$R_{21}$, other than hydrogen, optionally contain at least one heteroatom, and $R_{10}$-$R_{21}$, other than hydrogen, are optionally substituted, and wherein $L_1$ and $L_2$ bond with G through unsaturated sites.

15. The process of claim 14 comprising the step of removing the complex from the hydrosilylation product by magnetic separation and/or filtration.

16. The process of claim 14 wherein each occurrence of $R_{23}$ is independently

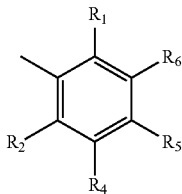

wherein $R_1$, $R_2$, $R_4$, $R_5$ and $R_6$ are as defined in claim 14.

17. The process of claim 14 wherein $R_1$ and $R_2$ in Formula (I) are both methyl, ethyl or n-propyl groups, and $R_1$ and $R_2$ in Formula (II) are both methyl, ethyl, n-propyl or isopropyl groups.

18. The process of claim 14 wherein $R_3$ is methyl.

19. The process of claim 14 wherein $R_{10}$, $R_{11}$, $R_{14}$, $R_{15}$, $R_{18}$ and $R_{20}$ are hydrogen.

20. The process of claim 14 wherein the complex is

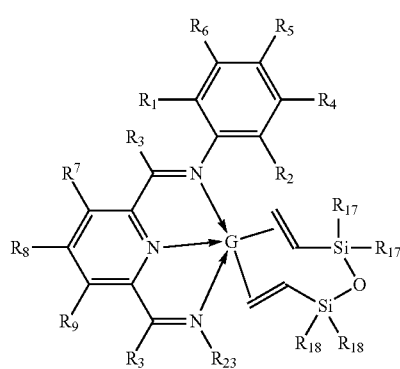

Formula (VI)

wherein G, $R_1$-$R_9$, $R_{17}$, $R_{18}$ and $R_{23}$ are as defined in claim 1.

21. The process of claim 14 wherein $R_{17}$ and $R_{18}$ are methyl groups.

22. The process of claim 14 wherein G is Fe.

23. The process of claim 14 wherein the complex is immobilized on a support.

24. The process of claim 23 wherein the support is selected from the group consisting of carbon, silica, alumina, $MgCl_2$, zirconia, polyethylene, polypropylene, polystyrene, poly(aminostyrene), dendrimers, and combinations thereof.

25. The process of claim 23 wherein at least one of $R_1$-$R_9$ contains a functional group that covalently bonds with the support.

26. The process of claim 14, wherein the silyl hydride is selected from the group consisting of $R_aSiH_{4-a}$, $(RO)_aSiH_{4-a}$, $Q_uT_vT_p^HD_wD_x^HM_y^HM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $H_gR'_{3-g}SiO_{1/2}$, M is $R'_3SiO_{1/2}$, each occurrence of R and R' is independently C1-C18 alkyl, C1-C18 substituted alkyl, wherein R and R' optionally contain at least one heteroatom, each occurrence of a independently has a value of from 1 to 3, g has a value of from 0 to 3, each of p, u, v, y and z is independently from 0 to 20, w and x are independently from 0 to 500, provided that p+x+y equals 1 to 500, and the valences of the all the elements in the silyl hydride are satisfied.

27. The process of claim 26, wherein each of p, u, v, y, and z is independently from 0 to 10, w and x are independently from 0 to 100, wherein p+x+y equals 1 to 100.

28. The process of claim 14, wherein the compound containing an unsaturated group is selected from the group consisting of an alkyl-capped allyl polyether, a vinyl functionalized alkyl-capped allyl or methylallyl polyether, a terminally unsaturated amine, an alkyne, a C2-C18 olefin, an unsaturated cycloalkyl epoxide, a terminally unsaturated acrylate or methyl acrylate, an unsaturated aryl ether, an unsaturated aromatic hydrocarbon, an unsaturated cycloalkane, a vinyl-functionalized polymer, a vinyl-functionalized silane, a vinyl-functionalized silicone, and combinations thereof.

29. The process of claim 14, wherein the compound containing an unsaturated group is a polyoxyalkylene having the generic formula:

$R^1(OCH_2CH_2)_z(OCH_2CHR^3)_w$—$OR^2$, Formula (VIII)

$R^2O(CHR^3CH_2O)_w(CH_2CH_2O)_z$—$CR^4{}_2$—$C\equiv C$—$CR^4{}_2$—$(OCH_2CH_2)_z(OCH_2CHR^3)_wR^2$ or (Formula X) or $H_2C=CR^4CH_2O(CH_2OCH_2)_z(CH_2OCHR^3)_w$ $CH_2CR^4=CH_2$ (Formula XI)

wherein each occurrence of $R^1$ is an unsaturated organic group containing from 2 to 10 carbon atoms, each occurrence of $R^2$ is independently hydrogen, vinyl, or a polyether capping group of from 1 to 8 carbon atoms, each occurrence of $R^3$ and $R^4$ are independently monovalent hydrocarbon groups, each occurrence of z is 0 to 100 inclusive, and each occurrence of w is 0 to 100 inclusive.

30. A process for preparing a silylated polyurethane comprising contacting a terminally unsaturated polyurethane polymer with a silyl hydride in the presence of a complex as defined in claim 14.

31. A composition produced from the process of claim 14 wherein the compound containing an unsaturated group is an alkyl-capped allyl polyether; and wherein the composition is essentially free of unreacted alkyl-capped allyl polyether and its isomerization products.

32. A composition produced from the process of claim 14 wherein the compound containing an unsaturated group is a terminally unsaturated amine, and wherein the composition is essentially free of unreacted terminally unsaturated amine and isomerization products, and wherein the product is essentially free of internal addition products.

33. A composition produced from the process of claim 14 wherein the compound containing at least one unsaturated group is a vinyl-functional silicone.

34. A process for the synthesis of a complex of Formula (I) as defined in claim 1 comprising the step of reacting a compound of Formula (V) with a reducing agent having a reduction potential more negative than −0.6 v versus ferrocene in the presence of nitrogen, wherein Formula (V) is

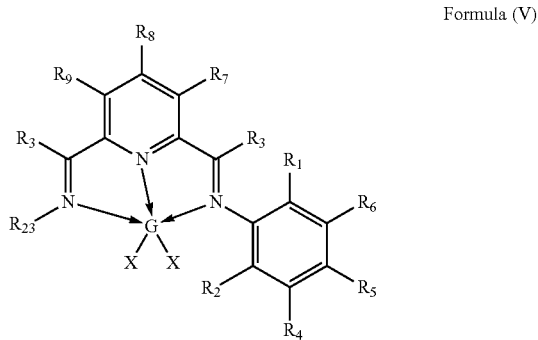

Formula (V)

wherein
G is Mn, Fe, Ni, or Co;
each occurrence of $R_1$, $R_2$, $R_3$, $R_4$, $R_5$, $R_6$, $R_7$, $R_8$ and $R_9$ is independently H, C1-18 alkyl, C1-C18 substituted alkyl, aryl, substituted aryl, or an inert group, wherein $R_2$-$R_9$, other than hydrogen, optionally contain at least one heteroatom;
$R_{23}$ is C1-C18 alkyl group or C1-C18 substituted alkyl, aryl or substituted aryl group, wherein $R_{23}$ optionally contains at least one heteroatom;
optionally any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure; and
X is an anion.

35. The process of claim 33 wherein the reducing agent is sodium naphthalenide.

36. The process of claim 33 wherein X is F, Cl, Br, I, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group.

37. A process for the synthesis of a complex of Formula (II) as defined in claim 1 comprising the step of reacting a complex of Formula (V) with $L_1$-$L_2$ wherein Formula (V) is

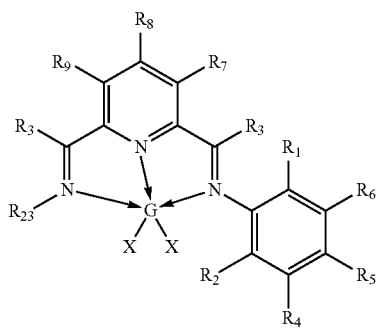

Formula (V)

wherein
G is Mn, Fe, Ni, or Co;
each occurrence of $R_1$, $R_2$, $R_3$, $R_4$, $R_5$, $R_6$, $R_7$, $R_8$ and $R_9$ is independently H, C1-18 alkyl, C1-C18 substituted alkyl, aryl, substituted aryl, or an inert group, wherein $R_2$-$R_9$, other than hydrogen, optionally contain at least one heteroatom;
$R_{23}$ is C1-C18 alkyl group or C1-C18 substituted alkyl, aryl or substituted aryl group, wherein $R_{23}$ optionally contains at least one heteroatom;
optionally any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure;
X is F, Cl, Br, I, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group; and $L_1$-$L_2$ is

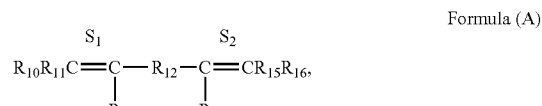

Formula (A)

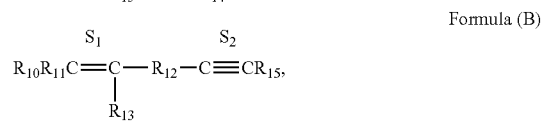

Formula (B)

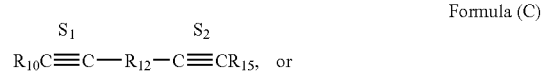

Formula (C)

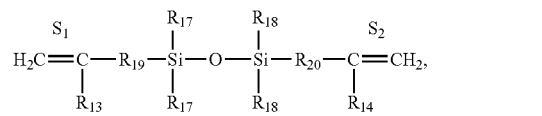

Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, C2-C18 alkynyl, or aryl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted,
each occurrence of $R_{12}$ is independently C1-C18 alkyl, C1-C18 substituted alkyl, C2-C18 alkenyl, C2-C18 substituted alkenyl, C2-C18 alkynyl, C2-C18 substituted alkynyl, aryl, or substituted aryl, wherein $R_{12}$ optionally contains at least one heteroatom;
optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;
each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together may optionally form a ring being a substituted or unsubstituted, saturated or unsaturated cyclic structure;
each occurrence of $R_{19}$ and $R_{20}$ is independently a covalent bond that connects Si and C, an alkyl, substituted alkyl or an heteroatom, wherein $R_{19}$, and $R_{20}$ optionally contain at least one heteroatom,
wherein $L_1$-$L_2$ bonds with G through unsaturated sites $S_1$ and $S_2$;
with the proviso that $L_1$-$L_2$ of Formula (A) is selected from the group consisting of 1,5-cyclooctadienes dicyclopentadienes, and norbornadienes.

38. The process of claim 14 wherein $R_2$ in Formula (I) is hydrogen, methyl, ethyl or isopropyl.

* * * * *